United States Patent [19]

Dundon et al.

[11] 4,455,435

[45] Jun. 19, 1984

[54] METHOD FOR THE PREPARATION OF LEUCO CRYSTAL VIOLET LACTONE

[75] Inventors: John P. Dundon, North Branch; Erwin Klingsberg, Mountainside, both of N.J.

[73] Assignee: American Cyanamid Company, Stamford, Conn.

[21] Appl. No.: 5,254

[22] Filed: Jan. 22, 1979

[51] Int. Cl.³ .................... C07D 307/78; C09B 11/10
[52] U.S. Cl. ..................................... 549/309; 260/391
[58] Field of Search ............................ 260/391, 343.4; 549/309

[56] References Cited

U.S. PATENT DOCUMENTS 2,726,252 12/1955 Balon et al. ........................ 260/391
3,739,000 6/1973 Lodolini et al. ................... 260/391

Primary Examiner—Ethel G. Love
Attorney, Agent, or Firm—Charles J. Fickey; Gordon L. Hart

[57] ABSTRACT

Leuco Crystal Violet Lactone is prepared by condensing one molar proportion of each of N,N-dimethylaniline, p-dimethylaminobenzaldehyde, and m-dimethylaminobenzoic acid with 0–1 molar proportion of urea and 1–4 molar proportions of a strong acidic condensing agent.

10 Claims, No Drawings

METHOD FOR THE PREPARATION OF LEUCO CRYSTAL VIOLET LACTONE

The present invention relates to novel methods for the preparation of leuco Crystal Violet Lactone (LCVL), chemically identified as 2-[4,4'-bis(dimethylamino)benzyhydryl]-5-dimethylaminobenzoic acid (I):

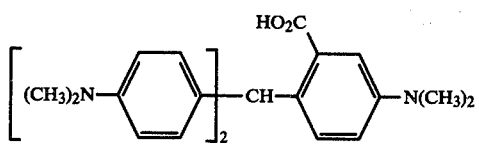

More particularly, it relates to a novel method for the preparation of LCVL wherein urea is incorporated into the reaction mixture to promote the reaction.

Leuco Crystal Violet Lactone may be readily oxidized by known chemical means to Crystal Violet Lactone (CVL), chemically identified as 3,3-bis(4-dimethylaminophenyl)-6-dimethylaminophthalide (II):

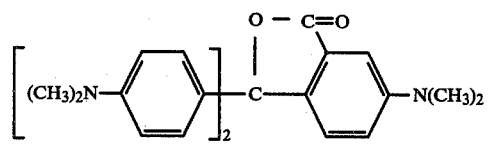

Both LCVL and CVL are well-known compounds (U.S. Pat. Nos. 2,417,897 and 2,458,328); the latter being commonly used in paper coating compositions for the manufacture of so-called carbonless carbon paper.

Leuco Crystal Violet Lactone is conventionally made by reaction of tetramethyl-4,4'-diaminobenzhydrol (III), commonly called Michler's Hydrol, with 3-dimethylaminobenzoic acid under acidic conditions:

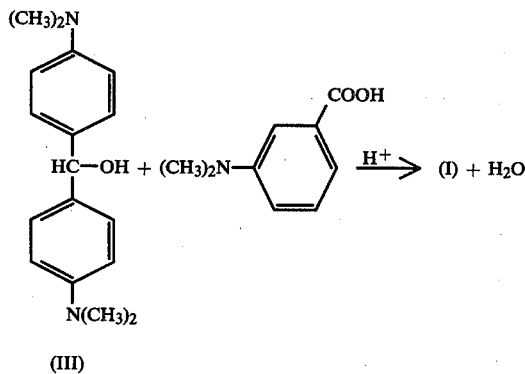

The resulting LCVL may then be oxidized to CVL (II) by any of a variety of known chemical procedures.

Since it is generally recognized that the yield and purity of Crystal Violet Lactone prepared by this method are dependent on the purity of the precursor LCVL, it has been common practice to isolate and purify the leuco compound before proceeding with the oxidation step. While it is possible to obtain pure CVL in this manner, the overall yield is low due to losses in isolation and purification. On the other hand, if the leuco compound is not isolated and purified before oxidation, the product (CVL) is generally impure and is obtained in low yield and requires further purification.

U.S. Pat. No. 4,076,728, recognizing this deficiency, provides a method for purification of the leuco compound in situ by extraction of the reaction mixture with an aromatic solvent or a mixture of an aromatic solvent and a water-immiscible alkane. This method reduces the aforementioned losses and provides the desired leuco compound in suitable purity for subsequent oxidation. The procedure is useful in the practice of the present invention and is incorporated herein by reference.

It has now been discovered that leuco Crystal Violet Lactone may be readily obtained by an in situ condensation of N,N-dimethylaniline, p-dimethylaminobenzaldehyde and m-dimethylaminobenzoic acid under the influence of a strong acidic condensing agent and, optionally, in the presence of urea.

It was found that Michler's Hydrol (III) reacts with urea to form an adduct which, when further condensed with m-dimethylaminobenzoic acid under acidic conditions, forms leuco Crystal Violet Lactone. This adduct, which may have the structure (IV) or (V), or a mixture thereof, is believed to form in the in situ reaction of the invention, thereby advantageously promoting the formation of leuco CVL.

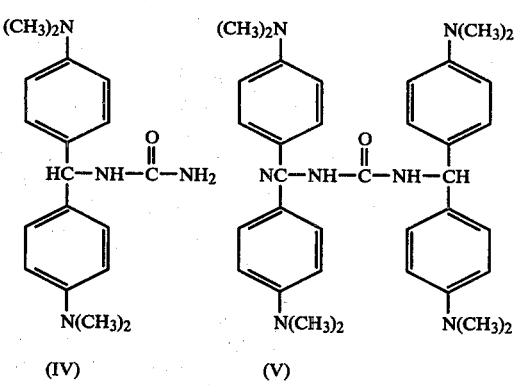

The present invention also encompasses the preparation of leuco Crystal Violet Lactone via the aforementioned adducts by reaction with m-dimethylaminobenzoic acid.

Michler's Hydrol may be reacted with from about 0.5 to 1.0 molar proportion of urea to form an adduct represented by (IV) or (V) which, in reality is a mixture of both the 1:1 and 2:1 adducts. Preferably one makes the adduct by reacting one molar proportion of Michler's Hydrol with about 0.5 molar proportion of urea. Leuco Crystal Violet Lactone is obtained readily when the adduct is condensed with m-dimethyl-aminobenzoic acid, in an amount equimolar with the Michler's Hydrol used in making the adduct, in the presence of a strong acidic condensing agent. The adduct is a solid and may be isolated and stored for later conversion to LCVL.

Preferably, leuco CVL is prepared in situ by reaction of essentially equimolar amounts of N,N-dimethylaniline, p-dimethylaminobenzaldehyde and m-dimethylaminobenzoic acid in the presence of 0 to 1 molar proportion of urea and 1 to 4 molar proportions of a strong acidic condensing agent at a temperature of about 60°–100° C., preferably about 90°–100° C.

Suitable strong acidic condensing agents are those preferably having a pKa of less than about 2.5, i.e. hydrochloric acid, sulfuric acid, p-toluenesulfonic acid, methanesulfonic acid, phosphorus trichloride, phosphorus pentachloride, and the like. Hydrochloric acid and sulfuric acid are preferred.

When the reaction is completed, a strong base, such as sodium hydroxide, is added to the reaction mixture in an amount sufficient to render the reaction mixture alkaline and form a salt of leuco CVL. The aqueous alkaline solution may then be extracted with an aromatic hydrocarbon solvent, such as toluene, or a mixture of an aromatic hydrocarbon solvent and a suitable water-immiscible alkane, such as heptane, in accordance with the procedure of the aforementioned U.S. Pat. No. 4,076,728. This extraction procedure removes impurities from the reaction mixture. The amount of extractant used is not critical so long as a sufficient amount is used to remove the impurities.

The extracted aqueous solution may then be acidified to a pH of about 5 to precipitate leuco CVL, which may then be filtered, washed with water, and dried, or the reaction mixture may be oxidized to Crystal Violet Lactone according to one of the well-known procedures, such as with potassium persulfate.

The following examples will serve to illustrate the invention.

EXAMPLE 1

Michler's Hydrol (135 grams, 0.5 mole) is dissolved in 500 ml of methanol at 50° C. To this is added a solution, at about 50° C., of 15 grams (0.25 mole) of urea in 100 ml of methanol. Concentrated hydrochloric acid (0.5 ml) is added to the yellow solution, which becomes deep blue. The acidified solution is heated for about 30 minutes at 55°–65° C. and the resulting crystals are filtered, washed with about 50 ml methanol, then with ammonium hydroxide to dissipate the blue color. The crystals are dried at 70° C. Yield 125 grams of Michler's Hydrolurea adduct.

EXAMPLE 2

A mixture of 18.2 grams of m-dimethylaminobenzoic acid and 25 grams (0.5 eq) of 98% sulfuric acid in 86 ml of water was heated to 65° C. The adduct of Example 1 (28.2 grams) was added and the reaction mixture was heated at 90°–95° C. for about 6.5 hours. The resulting yellow-green solution was poured into a mixture of ice and water. About 95 ml of 5N sodium hydroxide was added to bring the pH to 5.1 and the resulting solid material was filtered, washed with water and dried. There was obtained 41 grams (71% "real") of leuco Crystal Violet Lactone.

EXAMPLE 3

A solution of 20.5 grams (~0.05 mole) of leuco Crystal Violet Lactone from Example 2 in sodium hydroxide (12 grams of 50% NaOH in 250 ml water) is extracted twice with 100 ml of toluene at 60°–70° C. The extracted aqueous solution is heated to 60° C. and an aqueous solution of 15 grams of potassium persulfate in 150 ml of water is added thereto over 60 minutes. The resulting dark brown solids are filtered, washed with 150 ml of hot (60°–70° C.) water and dried. There is obtained 11.8 grams (56.9% yield) of Crystal Violet Lactone.

EXAMPLE 4

A mixture of 60 ml of concentrated hydrochloric acid (0.7 mol), 60 ml of water, 12 grams (0.2 mol) of urea, 30 grams (0.2 mol) of m-dimethylaminobenzoic acid, 25 ml (0.2 mol) of dimethylaniline and 35.8 grams (0.24 mol) of p-dimethylamino-benzaldehyde was heated at 90° C. for 5 hours. The mixture was cooled and neutralized with 280 ml of 5N sodium hydroxide, and extracted twice with 200 ml of toluene. The aqueous phase was separated from the toluene phase and divided into two equal portions. One-half was acidified with 5N hydrochloric and to pH 5 to precipitate leuco Crystal Violet Lactone, which was filtered, washed with water, and dried. There was obtained 26 grams (62.3% yield). The second portion was oxidized with 30.8 grams of potassium persulfate dissolved in 290 ml water, in the manner described in Example 3. There was obtained 13.2 grams (31.8%) of Crystal Violet Lactone.

EXAMPLE 5

A mixture of 53 grams of concentrated (98%) sulfuric acid, 175 ml of water, 30 grams of m-dimethylaminobenzoic acid, 35 ml of dimethylaniline and 35.8 grams of p-dimethyl-aminobenzaldehyde was heated at about 90° C. for 8 hours. The mixture was cooled and neutralized in a solution of 360 ml of 5N sodium hydroxide in 1800 ml of water. Toluene (200 ml) was added, the mixture was stirred at 50° C. and the aqueous layer separated from the organic layer. The aqueous layer was extracted again with 200 ml toluene and the layers separated. One-half of the aqueous layer (1130 grams) was acidified with 5N hydrochloric acid to precipitate the product at pH 5.8. There was obtained 11.5 grams of leuco Crystal Violet Lactone; yield 27.6%.

What is claimed is:

1. A method for the preparation of 2-[4,4'-bis(dimethylamino)benzhydryl]5-dimethylaminobenzoic acid (I):

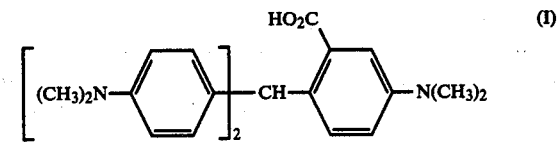

which comprises condensing essentially one molar proportion of each of N,N-dimethylaniline, p-dimethylaminobenzaldehyde and m-dimethylaminobenzoic acid with about 0.5 to 1 molar proportion of urea and about 1 to 4 molar proportions of a strong acidic condensing agent at a temperature of about 60°–100° C.

2. The method of claim 1 wherein said compound is recovered by (1) adding a base in an amount sufficient to render the reaction mixture alkaline and form the salt of (I); (2) extracting the alkaline reaction mixture with an aromatic hydrocarbon solvent, or a mixture thereof with a water-immiscible alkane, to remove impurities from said reaction mixture; and (3) acidifying said extracted reaction mixture to a pH of about 5, and (4) filtering said acidified mixture to recover the compound.

3. The method of claim 1 wherein said strong acidic condensing agent is selected from the group consisting of hydrochloric acid and sulfuric acid.

4. The method of claim 1 wherein said aromatic hydrocarbon solvent is toluene.

5. The method of claim 1 wherein said strong acidic condensing agent has a pKa of less than about 2.5.

6. A method for the preparation of 3,3-bis(4-dimethylaminophenyl)-6-dimethylaminophthalide (II):

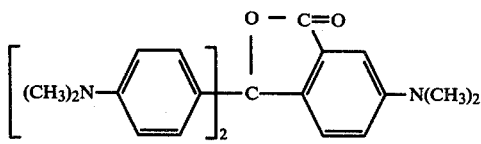 (II)

which comprises (1) condensing essentially one molar proportion of each of N,N-dimethylaniline, p-dimethylaminobenzaldehyde, and m-dimethylaminobenzoic acid with about 0.5 to 1 molar proportion of urea in the presence of about 1 to 4 molar proportions of a strong acidic condensing agent at a temperature of 60° to 100° C.; (2) adding a base thereto in an amount sufficient to render the reaction mixture alkaline and form the salt of 2-[4,4'-bis(dimethylamino)-benzhydryl]-5-dimethylaminobenzoic acid; (3) extracting the alkaline reaction mixture with an aromatic hydrocarbon solvent, or a mixture thereof with a water-immiscible alkane, to remove impurities from said reaction mixture; and (4) oxidizing with an oxidizing agent said reaction mixture to produce (II).

7. The method of claim 6 wherein said strong acidic condensing agent is selected from the group consisting of hydrochloric acid and sulfuric acid.

8. The method of claim 6 wherein said aromatic hydrocarbon solvent is toluene.

9. The method of claim 6 wherein said oxidizing is performed with an inorganic persulfate.

10. The method of claim 6 wherein said strong acidic condensing agent has a pKa of less than about 2.5.

* * * * *